United States Patent
Appenrodt et al.

(10) Patent No.: US 8,417,353 B2
(45) Date of Patent: Apr. 9, 2013

(54) METHOD AND APPARATUS FOR SECURING AN ELECTRODE

(75) Inventors: Peter Appenrodt, Bremen (DE); Frans L. H. Gielen, Eckelrade (NL); Paulus Cornelis van Venrooij, Hoensbroek (NL)

(73) Assignee: Medtronic, Inc., Minneapolis, MN (US)

( * ) Notice: Subject to any disclaimer, the term of this patent is extended or adjusted under 35 U.S.C. 154(b) by 970 days.

(21) Appl. No.: 12/432,291

(22) Filed: Apr. 29, 2009

(65) Prior Publication Data
US 2010/0280585 A1 Nov. 4, 2010

(51) Int. Cl.
*A61N 1/00* (2006.01)
*A61B 5/04* (2006.01)

(52) U.S. Cl.
USPC ............... 607/116; 607/139; 600/373

(58) Field of Classification Search .......... 600/373, 600/378; 607/116–117, 149, 45–46, 48, 607/139; 606/129–130
See application file for complete search history.

(56) References Cited

U.S. PATENT DOCUMENTS

| | | | |
|---|---|---|---|
| 4,328,813 A | 5/1982 | Ray | |
| 5,464,446 A | 11/1995 | Dreessen et al. | |
| 5,843,093 A | 12/1998 | Howard, III | |
| 5,843,146 A | 12/1998 | Cross, Jr. | |
| 5,865,842 A | 2/1999 | Knuth et al. | |
| 5,927,277 A | 7/1999 | Baudino et al. | |
| 6,044,304 A | 3/2000 | Baudino | |
| 6,134,477 A | 10/2000 | Knuteson | |
| 6,210,417 B1 | 4/2001 | Baudino et al. | |
| 6,321,104 B1 | 11/2001 | Gielen et al. | |
| 6,356,792 B1 | 3/2002 | Errico et al. | |
| 6,482,182 B1 | 11/2002 | Carroll et al. | |
| 6,493,573 B1 | 12/2002 | Martinelli et al. | |
| 6,516,212 B1 | 2/2003 | Bladen et al. | |
| 7,004,948 B1 | 2/2006 | Pianca et al. | |
| 8,043,304 B2 * | 10/2011 | Barker .................. | 606/129 |
| 2003/0114752 A1 | 6/2003 | Henderson et al. | |
| 2005/0049486 A1 | 3/2005 | Urquhart et al. | |
| 2005/0075680 A1 | 4/2005 | Lowry et al. | |

(Continued)

FOREIGN PATENT DOCUMENTS

EP 1048318 A2 11/2000
WO WO-2008119041 A1 10/2008

OTHER PUBLICATIONS

"Navigus, NexFrame, StimLoc", IGN—Image Guided Neurologics, copyright 2004, printed from www.igneurologics.com on Jul. 9, 2007, (2 sheets).

(Continued)

*Primary Examiner* — Christopher D Koharski
*Assistant Examiner* — Catherine Voorhees
(74) *Attorney, Agent, or Firm* — Harness, Dickey & Pierce, PLC (57) ABSTRACT

A system for securing at least one electrode to an anatomy is provided. The system can include a first plate, which can include at least one first passage. The at least one first passage can be configured to receive a lead of the at least one electrode. The system can also include a second plate configured to move relative to the first plate. The movement of the second plate relative to the first plate can at least partially occlude the at least one passage of the first plate to secure the lead of the at least one electrode to the anatomy.

14 Claims, 8 Drawing Sheets

U.S. PATENT DOCUMENTS

| | | | |
|---|---|---|---|
| 2005/0085714 A1 | 4/2005 | Foley et al. | |
| 2005/0085720 A1* | 4/2005 | Jascob et al. | 600/424 |
| 2005/0182420 A1* | 8/2005 | Schulte et al. | 606/130 |
| 2005/0192594 A1* | 9/2005 | Skakoon et al. | 606/129 |
| 2007/0233158 A1 | 10/2007 | Rodriguez | |
| 2008/0081982 A1 | 4/2008 | Simon et al. | |
| 2008/0103547 A1 | 5/2008 | Okun et al. | |
| 2008/0172068 A1 | 7/2008 | Adams et al. | |
| 2008/0269602 A1 | 10/2008 | Csavoy et al. | |
| 2009/0088826 A1* | 4/2009 | Bedenbaugh | 607/116 |

OTHER PUBLICATIONS

"Nexframe Reticle System, Trajectory Orientation," Medtronic, Inc. copyright 2006. (2 sheets).

"NexFrame System—Case: Bilateral Activa Lead Delivery to STN Using Nexframe," IGN Image Guided Neurologics, Inc. copyright 2004. Printed from www.igneurologics.com on Jul. 19, 2007. (2 sheets).

Leksell Stereotactic System® brochure, ELEKTA (undated) 6 pages.

Leksell Stereotactic System® http://www.elekta.com/healthcare_international_leksell_stereotactic_system.php (accessed May 20, 2009).

The Nexframe® System Stereotactic Technology brochure, Medtronic, (undated) 3 pages.

International Search Report and Written Opinion mailed Jun. 14, 2010 for PCT/US2010/023265, claiming benefit of U.S. Appl. No. 12/432,291, filed Apr. 29, 2009.

\* cited by examiner

METHOD AND APPARATUS FOR SECURING AN ELECTRODE

FIELD

The present disclosure relates to a surgical procedure, and particularly to a method and apparatus for securing at least one electrode to an anatomy, such as at least one deep brain stimulator (DBS) electrode.

BACKGROUND

The statements in this section merely provide background information related to the present disclosure and may not constitute prior art.

A surgical procedure can be performed on various portions of an anatomy, such as a human anatomy. The surgical procedures can be invasive to varying degrees, such as by performing an open procedure or by performing a less invasive procedure. A procedure can be performed in a less invasive manner by minimizing or attempting to minimize an incision or portal formed in the tissue of the anatomy, opening through bone, and other minimization techniques.

A less invasive procedure, however, can also reduce visualization of a portion of the anatomy upon which a procedure is occurring, reduce access with various instruments to a portion of the anatomy, and the like. The less invasive procedure may also require specialized and particular instruments to perform the procedure in an appropriate and beneficial manner. It is desirable, therefore, to provide instruments, procedures, and the like to achieve an optimal outcome while maintaining the less invasive procedure.

According to various applications, instruments can be guided with exterior guide tools or systems to a selected portion of the anatomy to perform the less invasive procedure. For example, at least one electrode can be guided into a portion of the anatomy, such as the brain, in a less invasive neurosurgical procedure. The at least one electrode can include a microelectrode (ME), semi-microelectrode, probe, deep brain stimulator (DBS), macroelectrode or combinations thereof. The ME, semi-microelectrode or macroelectrode can be used to record electrical activity within the brain, and the at least one probe, deep brain stimulator (DBS) electrode or macroelectrode can then be guided into the anatomy in an area of interest as indicated by the recording to deliver electrical therapy to the patient.

In certain instances, it may be desirable to couple or otherwise secure the at least one electrode to the anatomy, such that the effectiveness of the position of the at least one electrode can be monitored for a period of time. Accordingly, it would be desirable to provide methods and apparatuses for securing at least one electrode into an anatomy in a neurosurgical procedure.

SUMMARY

According to various embodiments, a system for securing at least one electrode to an anatomy is disclosed. The system can include a first plate. The first plate can include at least one first passage that can be configured to receive a lead of the at least one electrode. The system can also include a second plate configured to move relative to the first plate. The movement of the second plate relative to the first plate can at least partially occlude the at least one passage of the first plate to secure the lead of the at least one electrode to the anatomy.

Further disclosed is a system for securing at least one electrode to an anatomy. The system can include a base ring. The base ring can include at least one flange, which can couple the base ring to the anatomy, and a bore positionable over an access hole formed in the anatomy to enable at least one instrument to pass through the bore into the anatomy. The system can also include a first plate that includes at least one first passage and a coupling member that extends from a surface of the first plate. The first plate can be at least partially received within the bore of the base ring. The system can include a second plate, which can include a coupling feature that cooperates with the coupling member and at least one second passage that is coaxially aligned with the at least one first passage when the second plate is in a first position relative to the coupling member and is offset from the at least one first passage when the second plate is moved to a second position relative to the coupling member. The second plate can be at least partially received within the bore of the base ring in the second position. The system can further include a cover that is releasably coupled to the base ring to substantially enclose the bore, the first plate and the second plate when the second plate is in the second position.

Also disclosed is a method of securing at least one electrode to an anatomy. The method can include coupling at least one base having at least one passage about an opening formed in the anatomy, and positioning a lead of at least one electrode through the at least one passage of the base. The method can also include positioning the at least one electrode within the anatomy with the lead of the at least one electrode extending from the opening. The method can include coupling a top to the base so that the top at least partially occludes the at least one passage of the base to couple the lead of the at least one electrode to the base.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

The following description is merely exemplary in nature and is not intended to limit the present disclosure, application, or uses. It should be understood that throughout the drawings, corresponding reference numerals indicate like or corresponding parts and features. As indicated above, the present teachings are directed toward providing a system and method for securing at least one electrode for use with a neurosurgical procedure. It should be noted, however, that the present teachings could be applicable to any appropriate procedure in which it is desirable to couple, secure or hold an instrument relative to an anatomy. Therefore, it will be understood that the following discussions are not intended to limit the scope of the appended claims.

As will be discussed in greater detail herein, the present disclosure is directed toward a system and method for securing at least one electrode relative to an anatomy, such as a microelectrode, semi-microelectrode, macroelectrode, deep brain stimulator (DBS) electrode relative to a brain 96, to facilitate a surgical procedure on the anatomy. For example, a procedure on the brain 96 can include a recording device for detecting electrical activity in the brain 96, such as a microelectrode (ME), a semi-microelectrode, or a macroelectrode. Once a recording of the brain 96 has occurred, a stimulator probe, such as a deep brain stimulator (DBS) electrode or a macroelectrode can be delivered to an area identified with the ME, semi-microelectrode or macroelectrode. Generally, the ME, semi-microelectrode or macroelectrode, after identifying an area of interest in the brain 96, can be removed and the DBS electrode can be driven and guided along a similar or identical trajectory or axis relative to the removed ME, semi-microelectrode, or macroelectrode. Once the DBS probe is positioned within the anatomy, the DBS probe can be coupled, secured or fixed relative to the anatomy so that the DBS probe can electrically stimulate the selected region of the anatomy, either short term or long term.

In one example, it can be desirable to couple, secure or fix the DBS electrode to the anatomy for a selected period of time so that the affects of the electrical stimulation can be monitored. In this regard, due to the nature of the neurosurgical procedure, it can be desirable to evaluate the effectiveness of the electrical stimulation after the patient has recovered from the surgery. At this time, it may be desirable to re-position the at least one electrode within the anatomy, or it may be determined that the at least one electrode is properly positioned. If the at least one electrode is determined to be properly positioned, then the at least one electrode can be coupled, secured or fixed to the anatomy to enable short term or long term electrical stimulation of the anatomy. Thus, it can be desirable to provide a system or method for coupling, securing or fixing at least one electrode relative to the anatomy.

Figure 1:
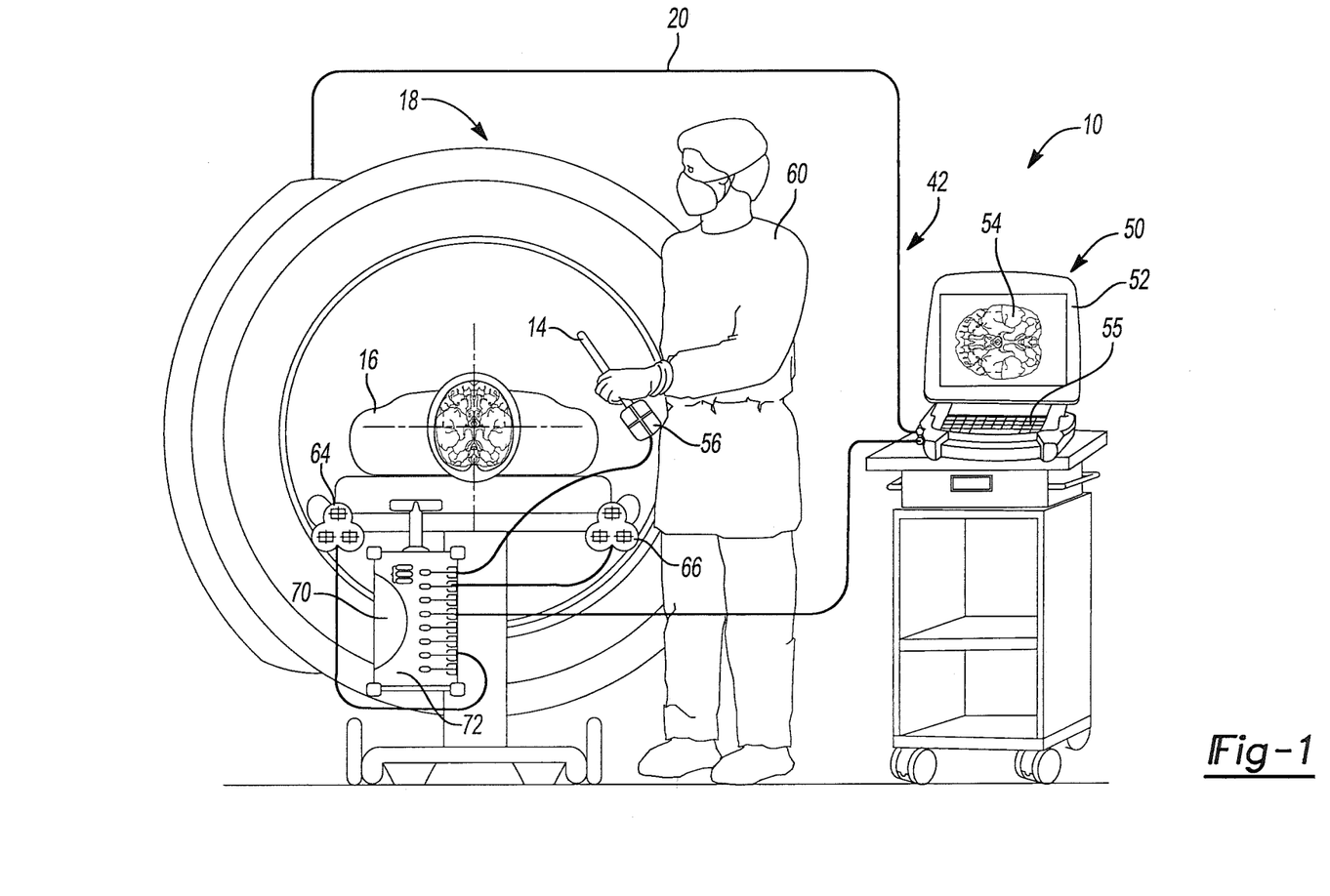
FIG. 1 is an environmental view of a surgical navigation system or computer aided surgical system for performing a surgical procedure, according to various embodiments.
Figure 2:
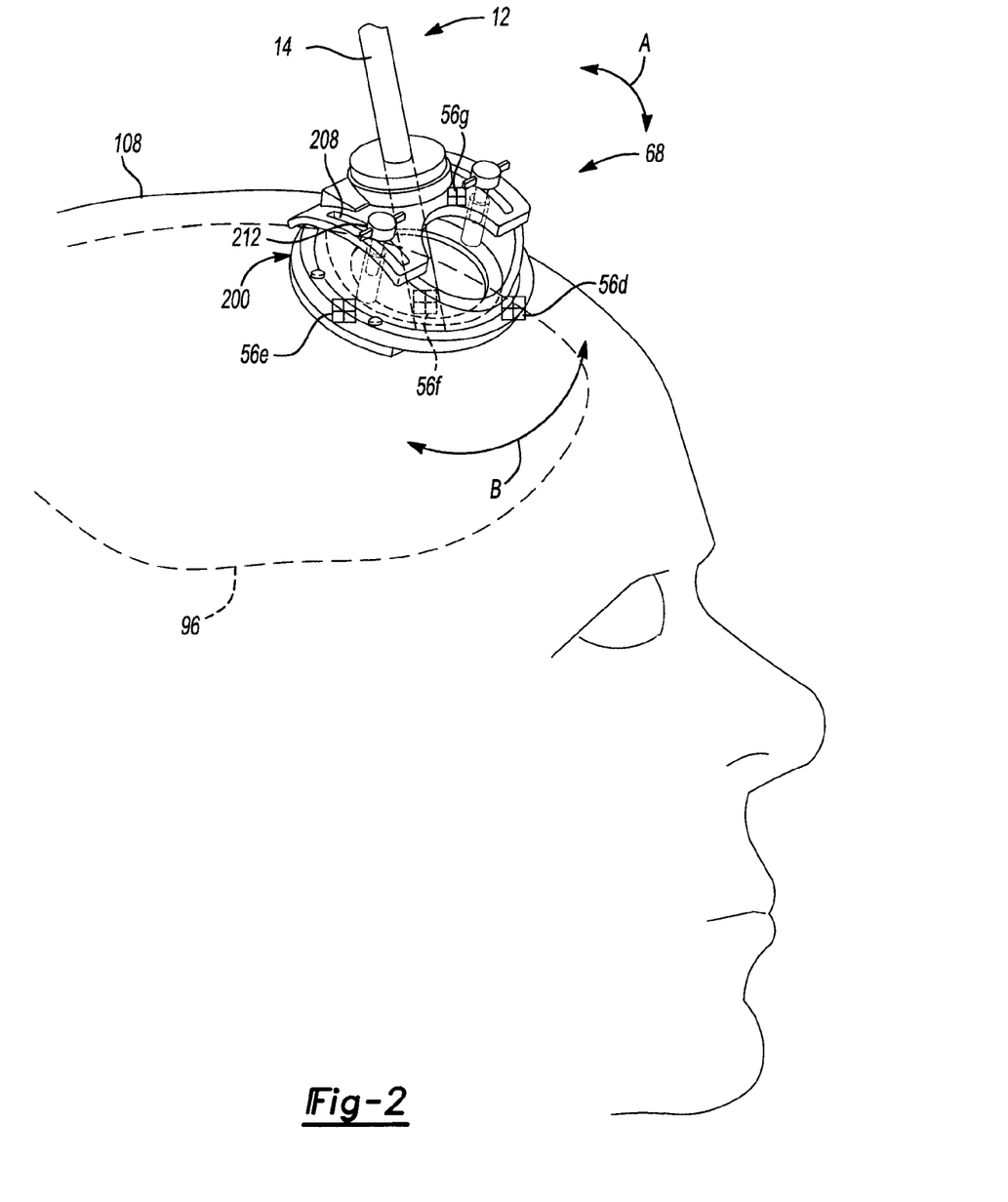
FIG. 2 is a detail environmental view of an exemplary dynamic reference frame (DRF) holder, for example, a head frame, for use with the navigation system of FIG. 1 according to various embodiments.

In one of various examples, in order to position the at least one electrode within the anatomy, such as the brain 96, with reference to FIGS. 1 and 2, the system and method can include an exemplary surgical navigation system 10 (FIG. 1), which can include a drive system 12 (FIG. 2) to control the insertion and withdrawal of one or more instruments 14 (FIG. 2) from the anatomy. Various surgical navigation systems can include those described in U.S. patent Ser. No. 10/651,267 (now U.S. Pat. App. Pub. No. 2005/0049486), and in currently pending U.S. patent Ser. No. 12/336,085, and the contents of both are incorporated herein by reference. As will be discussed, with reference to FIG. 2, the drive system 12 and the instruments 14 can be positioned relative to a dynamic reference frame, which can be coupled to a patient 16.

With reference to FIG. 1, the exemplary surgical navigation system 10 can include an image based system, an imageless system, an atlas or diagram based system, or combinations thereof. One skilled in the art will understand that the surgical navigation system 10 can require the registration of a patient 16, which defines patient space, to an image space, discussed further herein. According to various embodiments, registration can include registration between image space, defined by image data or atlas data, and the patient space.

With continued reference to FIG. 1, the navigation system 10 that can be used for various procedures is illustrated. The navigation system 10 can generally include an imaging device 18, such as a magnetic resonance imaging (MRI) device. For example, the intraoperative imaging system can include an MRI imaging system, such as the PoleStar® MRI or an O-arm™ imaging system sold by Medtronic, Inc. It will be understood that the navigation system 10 can incorporate or be used with any appropriate preoperatively or intraoperatively acquired image data. For example, various imageless systems can be used or images from atlas models can be used to produce patient images, such as those disclosed in U.S. Patent Pub. No. 2005-0085714, filed Oct. 16, 2003, entitled "Method and Apparatus for Surgical Navigation of a Multiple Piece Construct for Implantation," incorporated herein by reference.

The navigation system 10 can be used to track the location of an instrument 14, such as a probe or handpiece, relative to a patient 16 to assist in a surgical procedure. The probe 14 can have an electromagnetic (EM) instrument tracking device 56, which can receive a signal, transmit a signal, or combinations thereof to provide information to the navigation system 10 to determine a location of the instrument tracking device 56. It should be noted, however, that the use of an electromagnetic tracking device is merely exemplary, as any suitable tracking device could be employed, such as an infrared tracking device, or combinations thereof. A general discussion of the exemplary navigation system 42 is set forth in detail later herein.

The imaging device 18 can be used to acquire pre-, intra-, or post-operative or real-time image data of the patient 16. In one example, the imaging device 18 can be configured to acquire scans of the cranium 108 volumetrically in the mid-sagittal plane. The sequence of scans can have any suitable thicknesses such as five millimeters (mm) for example. The MRI sequence can be any suitable sequence such as T1, T2, IR, PD, etc. Image data 54 acquired with the imaging device 18 can be used by a workstation 50 as part of a control module or algorithm. The workstation 50 can also be used by a physician or user 60 to reference the image data 54 during an image-guided procedure.

With continued reference to FIG. 1, the workstation 50 can have a display device 52 to display image data 54 and a user interface 55. The workstation 50 can also include or be connected to an image processor, navigation processor, and a memory to hold instruction and data. The workstation 50 can also include an optimization processor that assists in a navigated procedure. The workstation 50 facilitates displaying the image data 54 as an image on the display device 52, saving, digitally manipulating, or printing a hard copy image of the received image data. The user interface 55, which may be a keyboard, mouse, touch pen, touch screen or other suitable device, allows the physician or user 60 to provide inputs to control the imaging device 18, or adjust the display settings of the display 52.

Image data can also be acquired using other imaging devices. For example, any 2D, 3D or 4D imaging device, such as isocentric fluoroscopy, bi-plane fluoroscopy, ultrasound, computed tomography (CT), multi-slice computed tomography (MSCT), positron emission tomography (PET), optical coherence tomography (OCT), intra-vascular ultrasound (IVUS), intra-operative CT, and others. Image data sets from hybrid modalities, such as positron emission tomography (PET) combined with CT, or single photon emission computer tomography (SPECT) combined with CT, could also provide functional image data superimposed onto anatomical data to be used to confidently reach target sites within the patient 16.

In one example, the navigation system 10 can comprise an electromagnetic navigation system, which can include a localizer, such as a coil array 64 and/or second tracking coil array 66, a coil array controller 70, and a navigation handpiece interface 72 can be used with a probe 44. The system 10 can also include dynamic reference frame, such as a head frame 68 (FIG. 2). Upon driving the coils in the coil array 64 with the coil array controller 68, electromagnetic fields are generated within the patient 16 in the area where the medical procedure is being performed, which is sometimes referred to as patient space. The electromagnetic fields generated in the patient space induce currents in at least one tracking device 56 positioned on or in the probe 44. Additionally or alternatively, at least one tracking device 56, and in this example, tracking devices 56d-g can be provided on the head frame 68 (FIG. 2).

These induced signals from the tracking device 56 can be delivered to the navigation handpiece interface 70 and subsequently forwarded to the coil array controller 68. The navigation handpiece interface 70 can also include amplifiers, filters and buffers to directly interface with the tracking device 56 in the probe 44. Additional details regarding surgical navigation may be found in commonly owned and currently pending U.S. patent Ser. No. 11/683,796, which is expressly incorporated herein by reference.

Thus, the navigation system 10 can be used to direct or guide one or more instruments 14 into the anatomy, such as one or more electrodes into the brain 96. With continued reference to FIG. 1 and with additional reference to FIG. 2, in one example, the navigation system 10 can include a guide or drive system 12 for use with the head frame 68. It should be noted that although a small scale stereotactic head frame 68 is illustrated herein, any suitable stereotactic head frame could be employed. For example, the stereotactic head frame can comprise any suitable stereotactic head frame known in the art, such as the Leksell Stereotactic System® provided by Elekta AB, and the small-scale head frame 68 can be any appropriate mechanism, such as the NEXFRAME™ sold by Medtronic Image Guided Neurologics of Minnesota, USA. Further detail regarding the head frame 68 can be found in U.S. patent Ser. No. 12/239,114, entitled "Method and Apparatus for Positioning a Guide Relative to a Base," and U.S. patent Ser. No. 12/110,666, entitled "Method and Apparatus for Performing a Navigated Procedure," which are incorporated herein by reference.

With reference to FIG. 2, the drive system 12 can include any appropriate drive system. The drive system 12 can be used to drive various instruments, such as one or more electrodes, into an anatomy, such as a brain 96. For example, the drive system 12 can comprise the microtargeting Drive® system produced by Fred Haer Corp., FHC Inc. of 9 Main Street, Bowdoinham Me. 04008, USA.

With reference to FIGS. 1 and 2, the drive system 12 can be interconnected with the head frame 68 to position the drive system 12 at any appropriate location to drive various instruments 14 into a cranium 108. The drive system 12 can also include one or more optional tracking devices 56 (FIG. 2), which can be used with the navigation system 10 to determine a position of the drive system 12 relative to the patient 16. In one example, the drive system 12 can be used with the navigation system 10 to drive various instruments, such as at least one electrode having a lead 202 (FIG. 3) into an anatomy, such as the brain 96.

Figure 3:
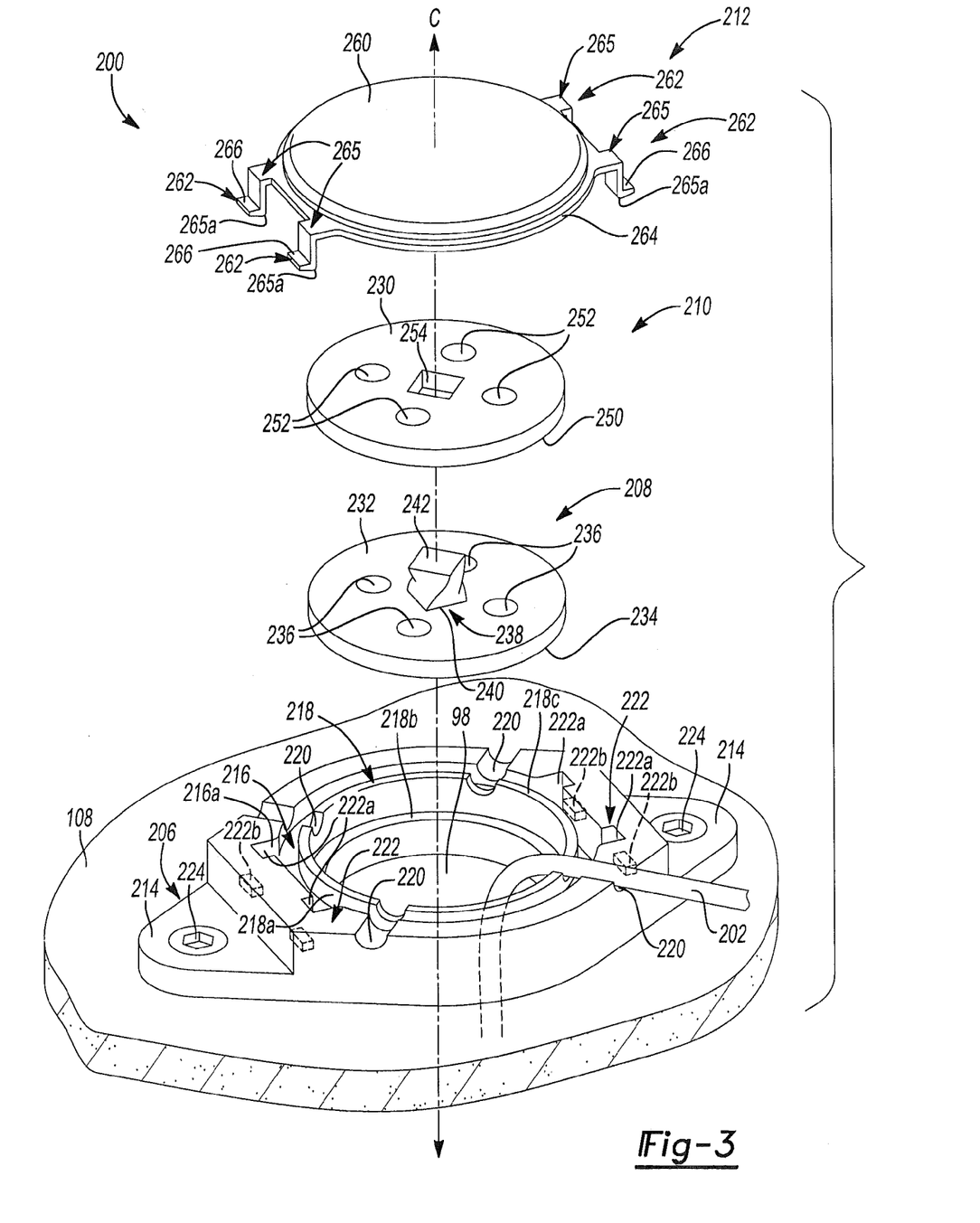
FIG. 3 is an exploded schematic illustration of an exemplary electrode fixation system for use during the surgical procedure performed with the surgical navigation system of FIG. 1.

Once the at least one electrode is properly positioned within the anatomy, with reference to FIG. 3, an electrode fixation system 200 can be used to couple, secure or fix the lead 202 of the at least one electrode to the cranium 108. The electrode fixation system 200 can couple, secure or fix at least one lead 202 of an electrode to the cranium 108, so that the electrode can remain properly positioned within the brain 96 for a desired length of time. As discussed, coupling, securing or fixing the lead 202 of the at least one electrode relative to the anatomy can enable the user 60 to evaluate the effectiveness of the electrical stimulation of the anatomy and verify that the at least one electrode is properly positioned within the anatomy prior to fixedly coupling the at least one electrode to the anatomy.

In one of various examples, the electrode fixation system 200 can include a base ring 206, a first or bottom plate 208, a second or top plate 210 and a cover 212. Each of the base ring 206, bottom plate 208, top plate 210 and cover 212 described and illustrated herein can be composed of a suitable biocompatible material, and generally can each be formed of a biocompatible polymeric material.

The base ring 206 can generally be coupled about the burr hole 98. In one example, the base ring 206 can comprise a base ring of a Stimloc™ lead anchoring device, which is commercially available from Medtronic, Inc. of Minneapolis, Minn. As the base ring 206 can comprise any suitable base for securing a lead or electrode to an anatomy known in the art, the base ring 206 will not be discussed in great detail herein. Briefly, however, the base ring 206 can be generally symmetric, and can include one or more fixation flanges 214, an annular channel 216, a circular bore 218, one or more radially extending guides 220 and one or more cover coupling members 222.

The fixation flanges 214 can comprise two flanges 214, which can extend from the base ring 206. Each of the flanges 214 can receive at least one mechanical fastener 224, which can be used to couple or fix the base ring 206 to the cranium 108. In one example, the flanges 214 can be positioned about opposite each other.

The annular channel 216 can be defined about a perimeter 218a of the bore 218. The annular channel 216 can receive a portion of the cover 212, which can aid in forming a tight closure between the base ring 206 and the cover 212. The annular channel 216 can include a perimeter 216a, and at least a portion of the guides 220 can be formed in the perimeter 216a.

The bore 218 can be defined or formed between the flanges 214, and can generally be formed about a center of the base ring 206. The bore 218 can define a passage, channel or conduit through which the surgeon can direct one or more instruments, such as the lead 202 of the at least one electrode, into the anatomy. The bore 218 can also include a shoulder or lip 218b, which can retain the bottom plate 208 and the top plate 210 within the bore 218. In one of various examples, the bore 218 can be sized such that a surface 230 of the top plate 210 is about planar with a surface 218c of the bore 218. It will be understood, however, that the bore 218 could be sized so that the surface 230 of the top plate 210 extends beyond or above the surface 218c of the bore 218, or so that the surface 230 of the top plate 210 is below the surface 218c of the bore 218, if desired.

At least a portion of the guides 220 can be defined in the perimeter 218a of the bore 218 and at least a portion of the guides 220 can be formed in the perimeter 216a of the channel 216. Generally, the guides 220 can direct an end of the at least one lead 202 through the bore 218, and out through the channel 216, away from the surgical site. This can enable the surgeon to continue working through the bore 218, without substantial interference from the at least one lead 202. The guides 220 can generally have a shape that can conform to the shape of the at least one lead 202, and in one example, the guides 220 can be concave to direct the lead 202 away from the bore 218.

The cover coupling members 222 can generally be defined between the guides 220 and adjacent to the flanges 214. The cover coupling members 222 can retain the cover 212 to the base ring 206, and thus, can comprise any suitable coupling mechanism that is capable of retaining a cover, such as a mechanical fastener, etc. In one example, each of the cover coupling members 222 can comprise a slot 222a and a detent 222b. The slot 222a can receive a first portion of the cover 212, and the detent 222b can be formed to receive a second portion of the cover 212, as will be discussed.

The bottom plate 208 and the top plate 210 can generally be received within the bore 218, and can be supported within the bore 218 by the lip 218b. It should be noted, that although the bottom plate 208 and top plate 210 are illustrated and described herein as being annular in shape, the bottom plate 208 and top plate 210 could have any desired shape, such as hemispherical, hexagon, octagon, etc. The bottom plate 208 can include a first or top surface 232, a second or bottom surface 234, at least one passage or bore 236 and a coupling member or post 238.

The top surface 232 can be opposite the bottom surface 234, and when the electrode fixation system 200 is assembled, the top surface 232 can be positioned adjacent to the top plate 210. The bottom surface 234 can be positioned adjacent to or in contact with the lip 218b of the bore 218 when the electrode fixation system 200 is assembled.

The at least one bore 236 can extend from the top surface 232 to the bottom surface 234, and can be sized to slidably receive the at least one lead 202. It should be noted that the bottom plate 208 can include any number of bores 236, and generally, the bottom plate 208 can include a number of bores 236 that corresponds to the number of leads 202 inserted into the cranium 108. In one example, the bottom plate 208 has four bores 236, but the bottom plate 208 could have one bore 236, five bores 236, etc. if desired. Generally, the bores 236 can be equally spaced about the bottom plate 208, however, the bores 236 could be spaced to correspond to the spacing of the guides 220 around the perimeters 216a, 218a of the channel 216 and bore 218, respectively. In one example, the at least one bore 236 can be radially offset from the post 238.

Figure 4:
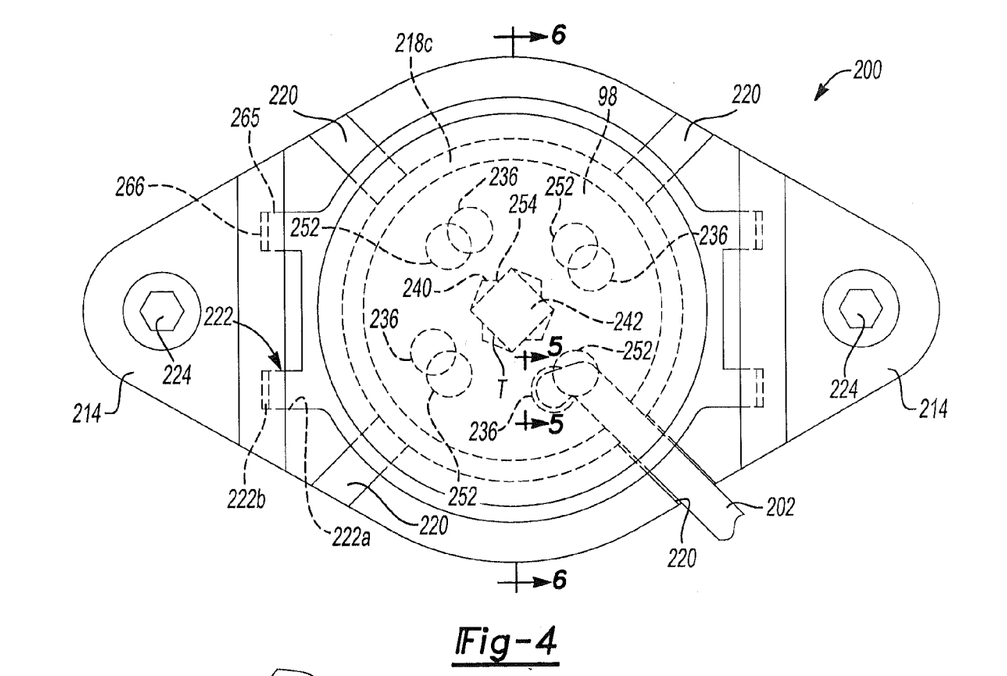
FIG. 4 is a top view of the electrode fixation system of FIG. 3.
Figures 5, 6:
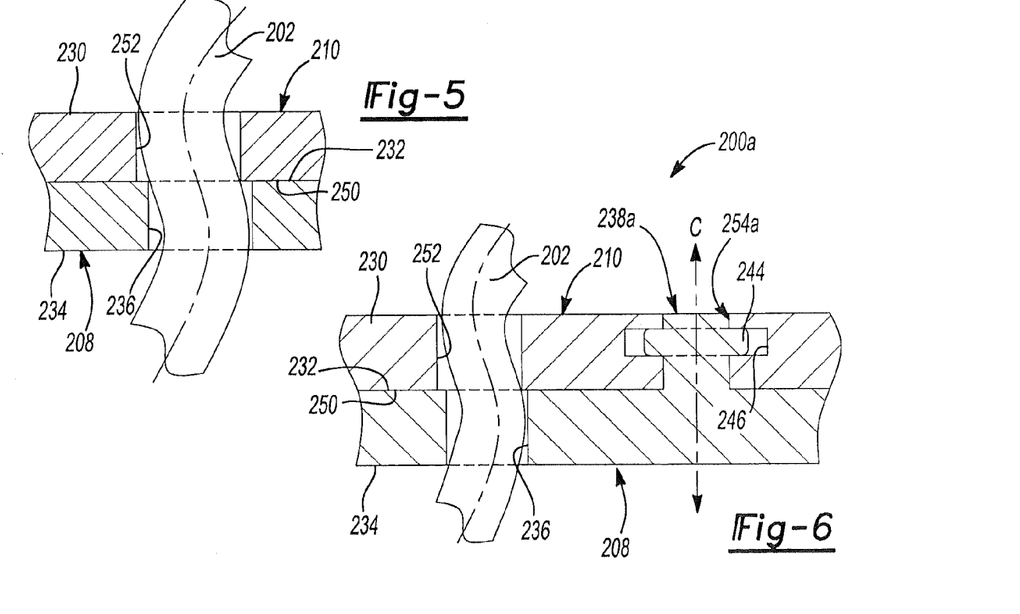
FIG. 5 is a cross-sectional schematic illustration of the electrode fixation system of FIG. 3 according to one of various examples, taken along line 5-5 of FIG. 3, illustrating at least one lead of an electrode secured to the anatomy.
FIG. 6 is a cross-sectional schematic illustration of the electrode fixation system of FIG. 3 according to one of various examples, taken along line 6-6 of FIG. 3, illustrating at least one lead of an electrode secured to the anatomy.

With reference to FIGS. 3-5, the post 238 can be coupled to the bottom plate 208. The post 238 can generally extend from the top surface 232. In one example, the post 238 can be formed about a centerline C of the bottom plate 208. The post 238 can include a first surface 240 and a second surface 242. The first surface 240 and the second surface 242 can have the same shape, and in one example, the first surface 240 and the second surface 242 can be square. It should be understood, however, that the first surface 240 and the second surface 242 could have any desired shape, such as rectangular, circular, triangular, trapezoidal, etc.

The first surface 240 of the post 238 can be coupled to the top surface 232 of the bottom plate 208, and the second surface 242 of the post 238 can be adjacent or about planar to the top surface 230 of the top plate 210 when the electrode fixation system 200 is assembled (FIGS. 4 and 5). In one example, the post 238 can have a twist, pitch or angular rotation T so that the first surface 240 of the post 238 can be angularly offset from the second surface 242 of the post 238 (FIG. 4). The twist, pitch or angular rotation T of the post 238 can enable the top plate 210 to rotate relative to the bottom plate 208 when the top plate 210 is assembled to the bottom plate 208. It should be understood, however, that the post 238 could be formed about a centerline C of the top plate 210, and the bottom plate 208 could be movable relative to the top plate 210, if desired.

With reference to FIGS. 3-5, the top plate 210 can include the first or top surface 230, a second or bottom surface 250, at least one passage or bore 252 and a coupling feature or bore 254. The top surface 230 can be opposite the bottom surface 250, and when the electrode fixation system 200 is assembled, the top surface 230 can be positioned adjacent to the cover 212 (FIG. 5). The bottom surface 250 can be positioned adjacent to the top surface 232 of the bottom plate 208 when the electrode fixation system 200 is assembled.

The at least one bore 252 can extend from the top surface 230 to the bottom surface 250, and can be sized to slidably receive the at least one lead 202. It should be noted that the top plate 210 can include any number of bores 252, and generally, the top plate 210 can include a number of bores 252 that corresponds to the number of leads 202 inserted into the cranium 108, and the number of bores 236 formed in the bottom plate 208. In one example, the top plate 210 has four bores 252, but the top plate 210 could have one bore 252, five bores 252, etc. if desired. Generally, the bores 252 can be equally spaced about the top plate 210, however, the bores 252 could be spaced to correspond to the spacing of the guides 220 around the perimeters 216a, 218a of the channel 216 and bore 218, respectively. Further, the bores 252 can be formed about the top plate 210 at a spacing that can be about equal to the spacing used to form the at least one bore 236 in the bottom plate 208. In one example, the at least one bore 252 can be radially offset from the coupling bore 254.

The coupling bore 254 can be formed about a centerline C of the top plate 210, and can extend from the top surface 230 to the bottom surface 250 of the top plate 210. The coupling bore 254 can generally have a shape that can enable the post 238 to be slidably received through the coupling bore 254. In one example, the coupling bore 254 can be substantially square. It will be understood, however, that that coupling bore 254 can have any desired shape that can cooperate with the post 238 to enable the top plate 210 to move relative to the bottom plate 208, such as circular, keyed, etc. The relative movement between the bottom plate 208 and the top plate 210 can couple, fix or secure the at least one lead 202 to the cranium 108, as illustrated in FIG. 5 and discussed in greater detail herein.

With reference to FIG. 4, the cover 212 can be coupled to the base ring 206 to enclose the bore 218, and thus, substantially prevent debris from entering the burr hole. As the cover 212 can comprise a cover associated with a Stimloc™ lead anchoring device, which is commercially available from Medtronic, Inc. of Minneapolis, Minn., the cover 212 will not be discussed in great detail herein. Briefly, however, the cover 212 can include a cap 260, one or more coupling members 262 and a sealing member 264.

With reference to FIGS. 3 and 4, the cap 260 can be annular, and can be sized to fit over the bore 218 of the base ring 206. The coupling members 262 can extend from either end of the cap 260, such that the coupling members 262 can matingly engage with the cover coupling members 222 of the base ring 206. Generally, the cover 212 can be secured to the base ring 206 through a snap-fit engagement between the coupling members 262 and the cover coupling members 222 of the base ring 206. In one example, each of the coupling members 262 can include a leg 265 and a flange 266. The leg 265 can extend from the cap 260, and the flange 266 can extend substantially perpendicular from an end 265a of the leg 265. The leg 265 can be sized to be slidably received into the slot 222a of the cover coupling members 222, while the flange 266 can be received within the detent 222b.

With reference to FIG. 3, the sealing member 264 can be formed about the cap 260. The sealing member 264 can extend from the cap 260 so that the sealing member 264 can be received into the channel 216 when the electrode fixation system 200 is assembled. The sealing member 264 can assist in maintaining a sterile environment within the bore 218.

In order to assemble the electrode fixation system 200 to the cranium 108, the base ring 206 can be positioned over the burr hole 98. The base ring 206 can be coupled to the cranium 108 by the mechanical fasteners 224, such as bone screws, which can be inserted through the bores 236 of the flanges 214. Then, at least one lead 202 can be inserted through the at least one bore 252 of the top plate 210 and the at least one bore 236 of the bottom plate 208. Generally, the top plate 210 and bottom plate 208 can be positioned or threaded onto the at least one lead 202 prior to the insertion of the at least one lead 202 into the anatomy, however, the top plate 210 and the bottom plate 208 can be positioned onto the at least one lead 202 after the at least one lead 202 is within the anatomy, if desired.

Once the at least one electrode has been inserted to a desired position within the brain 96, the bottom plate 208 can be advanced until the bottom plate 208 is in contact with the lip 218b of the bore 218. Then, the top plate 210 can be aligned with the bottom plate 208, and the top plate 210 can be advanced so that the coupling bore 256 can be positioned on the post 238. The top plate 210 can be moved from a first position adjacent to the second surface 242 of the post 238 to a second position adjacent to the first surface 240.

As the top plate 210 moves from the first position near the second surface 242 to the second position, near the first surface 240, the top plate 210 can rotate to move the bores 252 of the top plate 210 out of alignment with the bores 236 of the bottom plate 208 due to the twist, pitch or angular rotation T of the post 238. This shift in the alignment of the bores 236, 252 can cause the top plate 210 to at least partially occlude the bores 236 of the bottom plate 208, which can create a friction lock to couple, fix or secure the at least one lead 202 to the electrode fixation system 200, as illustrated in FIG. 5.

With the at least one lead 202 secured to the electrode fixation system 200, the head frame 68 can be removed, while maintaining the at least one electrode at the desired position within the brain 96. Then, the at least one lead 202 can be positioned in the desired one of the guides 220. Then, the cover 212 can be coupled to the base ring 206 to enclose the burr hole 98 (FIG. 4).

It should be understood that the coupling member or post 238 described and illustrated with regard to FIGS. 3-5 could be constructed somewhat differently to couple the top plate 210 to the bottom plate 208, while coupling, securing or fixing the lead 202 of the at least one electrode relative to the anatomy. In this regard, in one of various examples, as illustrated in FIG. 6, an alternative post 238a for use with an electrode fixation system 200a can include a resilient member 244, such as a rubber seal, formed about the post 238a. In this example, a coupling feature or bore 254a can define a channel 246, which can be sized to receive a portion of the resilient member 244. The resilient member 244 cooperates with the channel 246 to further secure the top plate 210 to the bottom plate 208 and to resist the lateral movement of the top plate 210 relative to the bottom plate 208.

Figure 7:
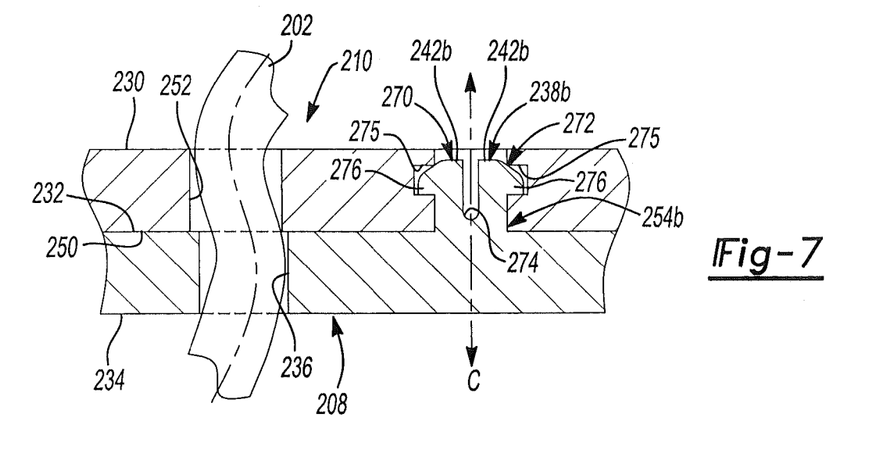
FIG. 7 is a cross-sectional schematic illustration of the electrode fixation system of FIG. 3 according to one of various examples, taken along line 6-6 of FIG. 3, illustrating at least one lead of an electrode secured to the anatomy.

With reference to FIG. 7, an alternative coupling member or post 238b for use with an electrode fixation system 200b, according to various examples, can comprise a first member 270 and a second member 272, which can be separated by a slot 274. The first member 270 and second member 272 can be resilient, yet flexible, so that the first member 270 and second member 272 can each move relative to the other during the assembly of the top plate 210 to the bottom plate 208. In one example, the first member 270 and second member 272 can each include an angular projection 276, which can engage a channel 275 formed in a coupling feature or bore 254b of the top plate 210. The first member 270 and the second member 272 can cooperate with the coupling bore 254b to provide a snap-fit engagement between the top plate 210 and the bottom plate 208. Note that in this one of various examples, a second surface 242b of the post 238b does not extend beyond the top surface 230 of the top plate 210.

Figure 8:
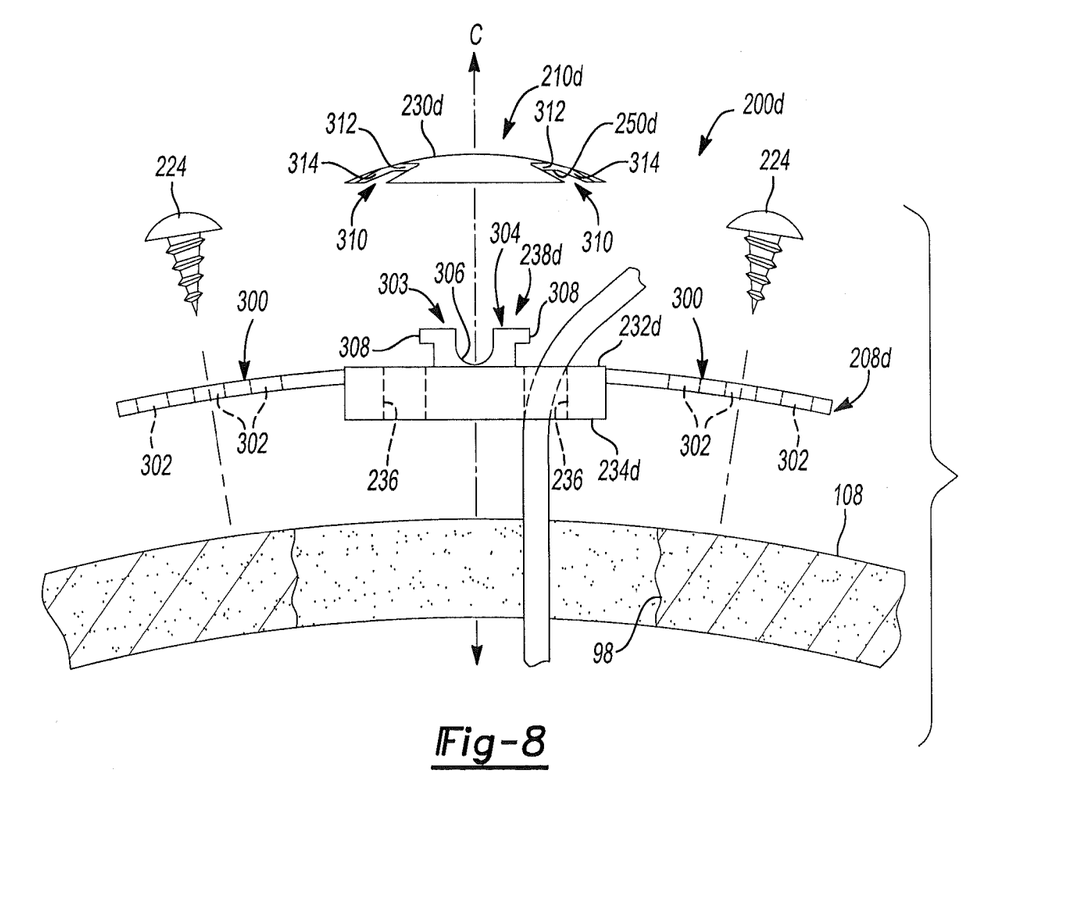
FIG. 8 is an exploded schematic illustration of an exemplary electrode fixation system for use during the surgical procedure performed with the surgical navigation system of FIG. 1 according to one of various examples.
Figure 9:
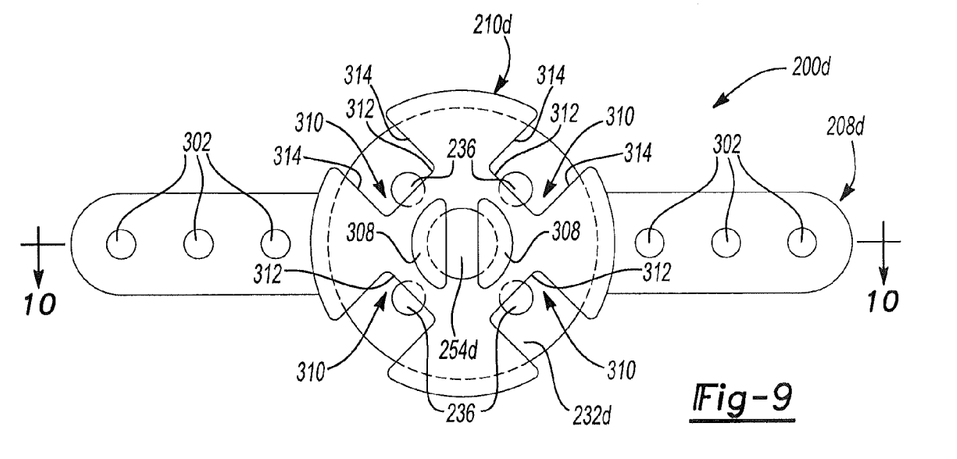
FIG. 9 is a top view of the electrode fixation system of FIG. 8.
Figure 10:
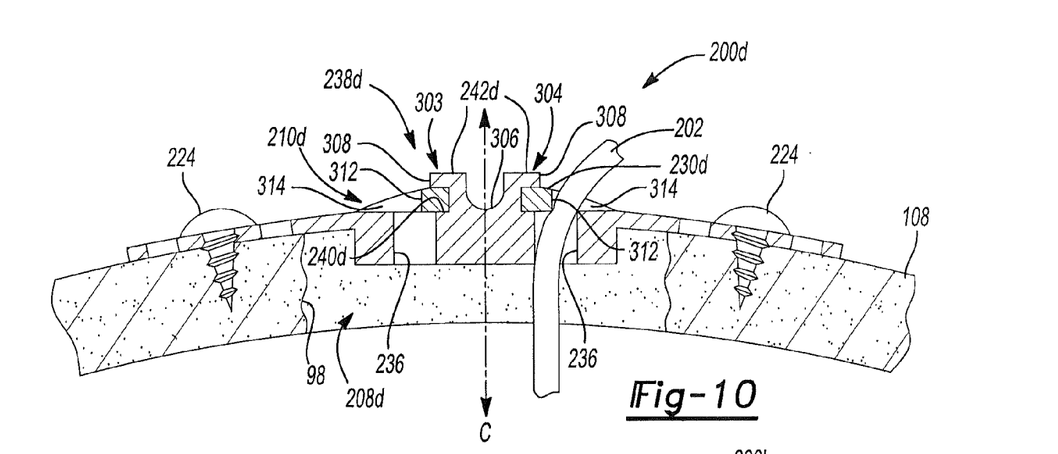
FIG. 10 is a cross-sectional schematic illustration of the electrode fixation system of FIG. 8 according to one of various examples, taken along line 10-10 of FIG. 9, illustrating at least one lead of an electrode secured to the anatomy.

With reference to FIGS. 8-10, in one example, an electrode fixation system 200d can include a first or bottom plate 208d and a second or top plate 210d. As the bottom plate 208d and the top plate 210d can be similar to the bottom plate 208 and top plate 210 described with regard to FIGS. 3-5, only the differences between the bottom plate 208 and the bottom plate 208d, and the top plate 210 and the top plate 210d, will be discussed in great detail herein, and the same reference numerals will be used to denote the same or similar components.

In this example, with reference to FIGS. 8-10, the bottom plate 208d can be coupled about the burr hole 98. The bottom plate 208d can generally be symmetric about a horizontal axis and a vertical axis. The bottom plate 208d can include a first or top surface 232d, a second or bottom surface 234d, one or more flanges 300, the at least one bore 236 and a coupling member or post 238d. The top surface 232d can be opposite the bottom surface 234d, and when the electrode fixation system 200d is assembled, the top surface 232d can be positioned adjacent to and in contact with the top plate 210d. The bottom surface 234d can extend into the burr hole 98 when the electrode fixation system 200d is coupled to the cranium 108. In other words, the bottom surface 234d can be stepped such that the bottom surface 234d can extend below a surface of the cranium 108 to be positioned within the burr hole 98.

The flanges 300 can comprise two flanges 300, which can extend outwardly from the bottom plate 208d generally planar to the top surface 232a. In one example, the flanges 300 can be elongated and rectangular in shape, however, the flanges 300 could have any desired shape. Generally, the flanges 300 can be flexible to enable the flanges 300 to conform with the anatomy. Each of the flanges 300 can define a plurality of bores 302, which can each receive a suitable biocompatible mechanical fastener 224, such as a bone screw. The plurality of bores 302 can enable the user to select a desired one bore 302 to use to couple the bottom plate 208d to the burr hole 98, which can enable the surgeon to customize the bottom plate 208d for each unique procedure. In addition, if desired, the unused or unselected bores 302 distal of the selected bore 302 can be separated from the flanges 300, via cutting the flanges 300, for example. In one example, the flanges 300 can be positioned about opposite each other.

The post 238d can be coupled to the bottom plate 208d. The post 238d can generally extend from the top surface 232d. In one example, the post 238d can be formed about a centerline C of the bottom plate 208d. The post 238d can include a first member 303 and a second member 304, which can be separated by a slot 306. The first member 303 and second member 304 can be resilient, yet flexible, so that the first member 303 and second member 304 can each move relative to the other during the assembly of the top plate 210d to the bottom plate 208d. In one example, with reference to FIG. 10, the first member 303 and second member 304 can each include a first surface 240d, which can be opposite a second surface 242d and a lip 308. The first surface 240d can be coupled to the top surface 232 of the bottom plate 208d, and the lip 308 can be formed at a second surface 242d. The lip 308 can extend beyond a first or top surface 230d of the top plate 210d when the top plate 210d is assembled to the bottom plate 208d. The lip 308 can secure the top plate 210d to the bottom plate 208d, and can also cooperate with the top plate 210d to apply a compressive force on the at least one lead 202, as will be discussed further herein.

With reference to FIGS. 8-10, the top plate 210d can be generally concave, and can include the first or top surface 230d, a second or bottom surface 250d, a coupling feature or bore 254d (FIGS. 9 and 10) and at least one lead guide 310. The top surface 230d can be opposite the bottom surface 250d, and when the electrode fixation system 200d is assembled, the lip 308 of the post 238d can be in contact with the top surface 230d (FIG. 9). The contact between the lip 308 and the top surface 230d can cause the top plate 210d to be compressed from a generally concave shape having a first radius (FIG. 8) to a generally concave shape having a second radius (FIG. 10), which is larger than the first radius. The bottom surface 250d can be positioned adjacent to the top surface 232d of the bottom plate 208d when the electrode fixation system 200d is assembled (FIG. 10).

With reference back to FIGS. 8-10, the coupling bore 254d can be formed about a centerline C of the top plate 210d (FIG. 10), and can extend from the top surface 230d to the bottom surface 250d of the top plate 210d. The coupling bore 254d can generally have a shape that can enable the post 238d to be slidably received through the coupling bore 254d. In one example, the coupling bore 254d can be substantially circular. It will be understood, however, that that coupling bore 254d can have any desired shape that can cooperate with the post 238d to enable the top plate 210d to be coupled to the bottom plate 208d, such as circular, keyed, etc.

With reference to FIGS. 8-10, the at least one lead guide 310 can be formed generally radially offset from the centerline C of the top plate 210d. Generally, the at least one lead guide 310 can define a cut-out through the top plate 210d, and in one of various examples, the at least one lead guide 310 can comprise a cut-out having an occluding or back wall 312 and a pair of opposed side walls 314. The at least one lead guide 310 can generally be formed in the top plate 310d so that the back wall 312 can at least partially occlude the at least one bore 236 of the bottom plate 208d. It should be noted that the top plate 210d can include any number of lead guide(s) 310, and generally, the top plate 210d can include a number of lead guide(s) 310 that corresponds to the number of leads 202 inserted into the cranium 108, and the number of bores 236 formed in the bottom plate 208d. In this example, the top plate 210d has four lead guides 310, but the top plate 210d could have one lead guide 310, five lead guides 310, etc. if desired. Generally, as illustrated, the lead guides 310 can be equally spaced about the top plate 210d, and typically can be spaced so that the back wall 312 of each of the lead guides 310 can at least partially occlude each bore 236 formed in the bottom plate 208d.

In order to assemble the electrode fixation system 200d to the cranium 108, the bottom plate 208d can be positioned over the burr hole 98. The surgeon can select the desired bores 302 of the flanges 300 for coupling the bottom plate 208d over the burr hole 98. Once the desired bores 302 are selected, the surgeon can optionally remove the excess bores 302 from the flanges 300. Then, the surgeon can insert the mechanical fasteners 224 to couple the bottom plate 208d to the cranium 108 (FIG. 8).

Then, with the at least one electrode coupled to the drive system 12, the at least one lead 202 of the at least one electrode can be inserted through the at least one bore 236 of the bottom plate 208d. Once the at least one electrode has been inserted to a desired position within the brain 96, the top plate 210d can be aligned with the bottom plate 208d so that the coupling bore 254d can be positioned adjacent to the post 238d such that the lead guide(s) 310 are aligned with the at least one bore 236 of the bottom plate 208d. The top plate 210d can be moved from a first position near the second surface 242d of the post 238d to a second position near the first surface 240d of the post 238d.

As the top plate 210d moves from the first position to the second position, the first member 303 and the second member 304 can be moved or compressed towards each other until the lip 308 of the first member 303 and the second member 304 contact the top surface 230d of the top plate 210d. This engagement between the lip 308 and the top surface 230d of the top plate 210d can cause the back wall 312 to contact the at least one lead 202 within the at least one bore 236 and apply a force to the at least one lead 202 (FIG. 10). The force applied by the top plate 210d can couple, fix or secure the at least one lead 202 to the electrode fixation system 200d. With the at least one lead 202 coupled, secured or fixed to the anatomy, the head frame 68 can be removed, while the at least one electrode remains at a desired location within the brain 96.

It should be noted that the post 238d of the electrode fixation system 200d could be constructed somewhat differently. In this regard, with reference to FIG. 10A, a post 238h can include a lip 308h and a groove 305. The lip 308h can be formed to have a thickness T1. As the top plate 210h and bottom plate 208h can be similar to the top plate 210d and the bottom plate 208d described with regard to FIGS. 8-10, only the differences will be discussed in great detail herein, and the same reference numerals will be used to denote the same or similar components. In addition, for ease of illustration, a cross-sectional view of the electrode fixation system 200h is provided, with the understanding that the electrode fixation system 200h can be substantially similar to the electrode fixation system 200d with the exception of the lip 308h.

Figure 10A:
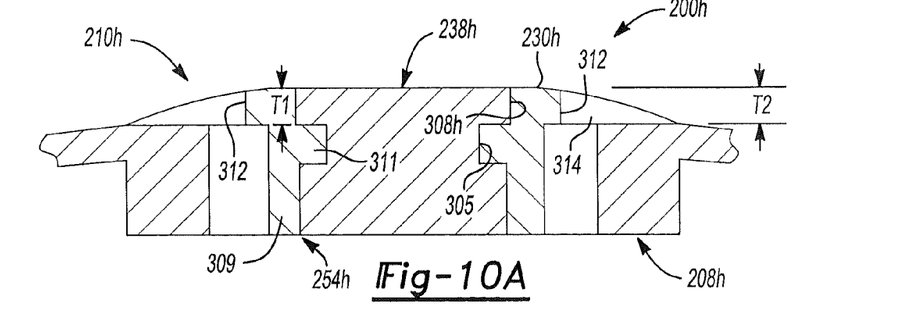
FIG. 10A is a cross-sectional schematic illustration of an electrode fixation system similar to the electrode fixation system of FIG. 8, illustrating one exemplary connection between an exemplary top plate and an exemplary bottom plate.

With continued reference to FIG. 10A, the thickness T1 of the lip 308h can be about substantially equal to a thickness T2 of a top surface 230h of a top plate 210h. The about equal thickness T1, T2 of the lip 308h and the top plate 210h can provide for a flush or level surface when the top plate 210h is coupled to a bottom plate 208h. The level surface of the top plate 210h can allow an anatomy, such as a skin flap, to be smoothly positioned over the top plate 210h. The groove 305 can be formed under the lip 308h, and can cooperate with the lip 308h to couple the top plate 210h to a bottom plate 208h, as will be discussed.

In the example of FIG. 10A, the top plate 210h can include a coupling bore 254h. The coupling bore 254h can include a sidewall 309 and a lip 311. The sidewall 309 can guide the coupling bore 254h into engagement with the post 238d. The lip 311 can be annular, and can extend from the sidewall 309 into the coupling bore 254h. The lip 311 can be positioned on the sidewall 309 at a location that can enable the lip 311 to engage the groove 305. In this regard, in order to couple the top plate 210h to the bottom plate 208h, the top plate 210h can be positioned relative to the bottom plate 208h such that the coupling bore 254h is aligned with the lip 308h. Then, the sidewall 309 of the coupling bore 254h of the top plate 210h can be positioned over the lip 308h, and the top plate 210h can be advanced until the lip 311 of the coupling bore 254h engages the groove 305 of the post 238h. This can enable the top plate 210h to be coupled to the bottom plate 208h while maintaining a level surface for receipt of an anatomy, such as a skin patch.

Figure 11:
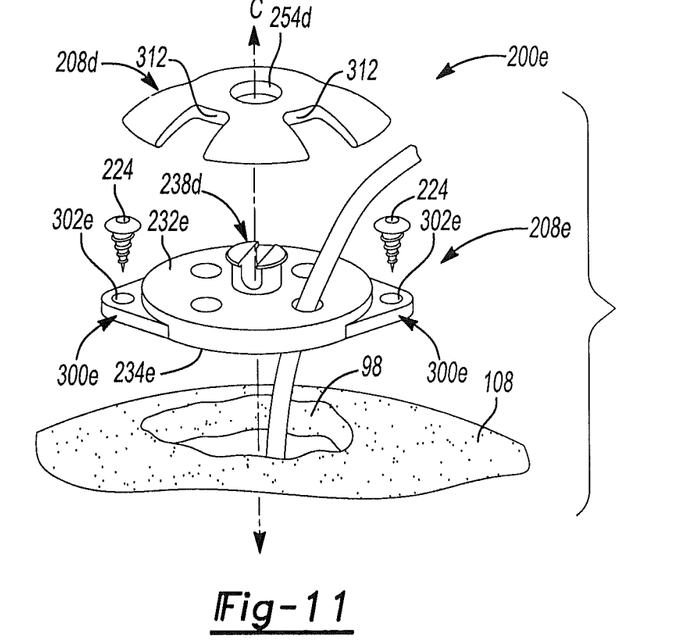
FIG. 11 is an exploded schematic illustration of an exemplary electrode fixation system for use during the surgical procedure performed with the surgical navigation system of FIG. 1 according to one of various examples.
Figure 12:
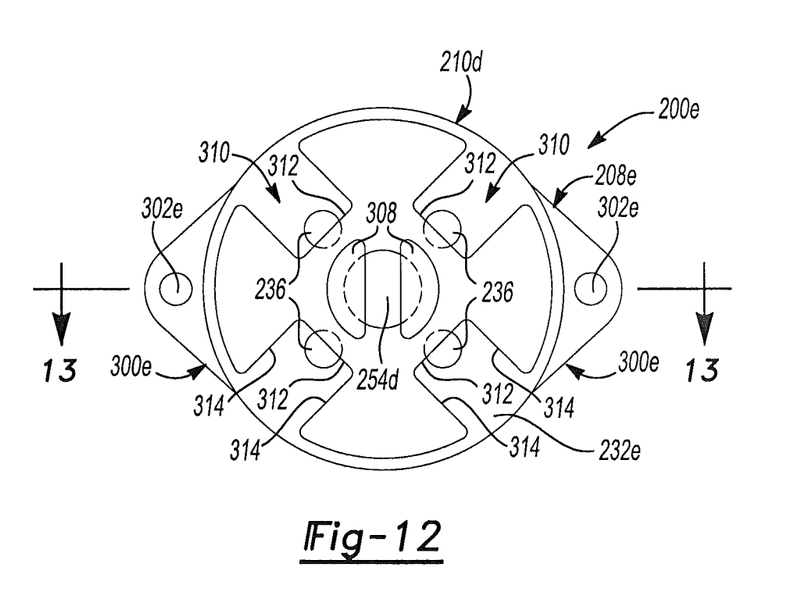
FIG. 12 is a top view of the electrode fixation system of FIG. 11.
Figure 13:
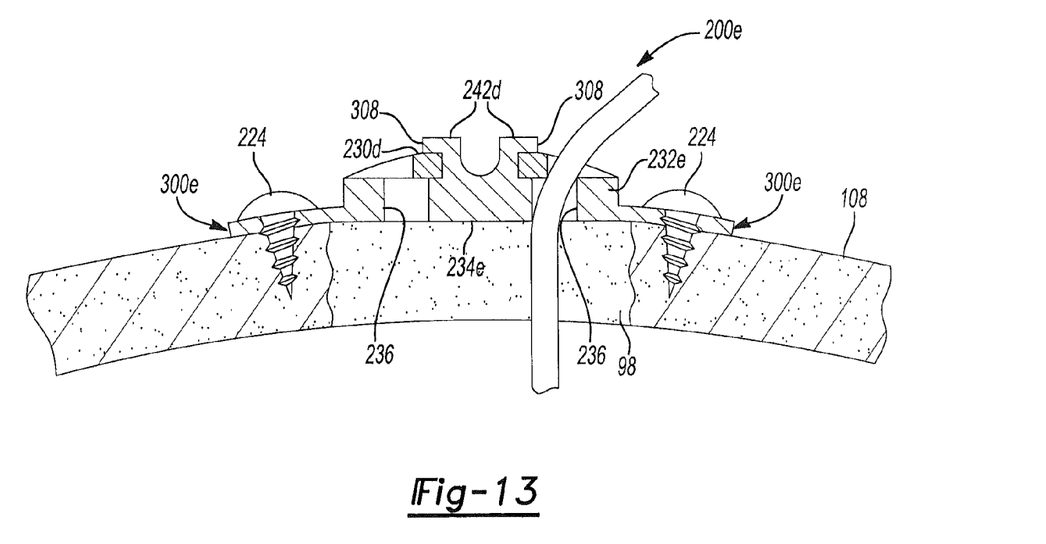
FIG. 13 is a cross-sectional schematic illustration of the electrode fixation system of FIG. 11 according to one of various examples, taken along line 13-13 of FIG. 12, illustrating at least one lead of an electrode secured to the anatomy.

With reference to FIGS. 11-13, in one example, an electrode fixation system 200e can include a first or bottom plate 209e and the second or top plate 210d. As the bottom plate 209e can be similar to the bottom plate 208d described with regard to FIGS. 8-10, only the differences between the bottom plate 209e and the bottom plate 208d, will be discussed in great detail herein, and the same reference numerals will be used to denote the same or similar components.

In this example, the bottom plate 209e can be coupled about the burr hole 98. The bottom plate 209e can generally be symmetric about a horizontal axis and a vertical axis. The bottom plate 209e can include a first or top surface 232e, a second or bottom surface 234e, one or more flanges 300e, the at least one bore 236 and the coupling member or post 238d. The top surface 232e can be opposite the bottom surface 234e, and when the electrode fixation system 200e is assembled, the top surface 232e can be positioned adjacent to and in contact with the top plate 210e. The bottom surface 234e can span the burr hole 98, and generally, does not extend into the burr hole 98, when the electrode fixation system 200e is coupled to the cranium 108. In other words, in this example, the top surface 232e can be stepped.

The flanges 300e can comprise two flanges 300e, which can extend outwardly from the bottom plate 209e. In one example, the flanges 300e can be arcuate in shape, however, the flanges 300e could have any desired shape. Each of the flanges 300e can define a bore 302e, which can receive a suitable biocompatible mechanical fastener 224, such as a bone screw. In one example, the flanges 300e can be positioned about opposite each other.

In order to assemble the electrode fixation system 200e to the cranium 108, the bottom plate 209e can be positioned over the burr hole 98. The surgeon can insert the mechanical fasteners 224 into the bores 302e of the flanges 300e to couple the bottom plate 209e to the cranium 108. Then, the at least one lead 202 can be inserted through the at least one bore 236 of the bottom plate 209e. With the at least one lead 202 inserted through the at least one bore 236 of the bottom plate 209e, the at least one electrode can be inserted to a desired position within the brain 96.

Once the at least one electrode has been inserted to a desired position within the brain 96, the top plate 210e can be aligned with the bottom plate 208d so that the coupling bore 256d can be positioned adjacent to the post 238d such that the lead guide(s) 310 are aligned with the at least one bore 236 of the bottom plate 209e. The top plate 210 can be moved from a first position near the second surface 242d of the post 238d to a second position near the first surface 240d of the post 238d. As discussed, the engagement between the lip 308 and the top surface 230d of the top plate 210d can cause the back wall 312 to contact the at least one lead 202 within the at least one bore 236 of the bottom plate 209e to couple, fix or secure the at least one lead 202 to the electrode fixation system 200d. With the at least one lead 202 coupled, fixed or secured to the anatomy, the head frame 68 can be removed, while the at least one electrode remains within the brain 96.

Figure 14:
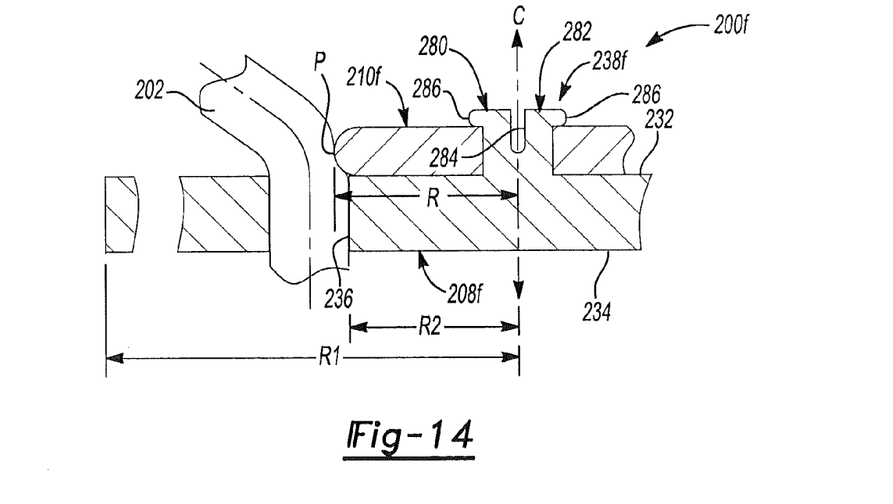
FIG. 14 is a cross-sectional schematic illustration of the electrode fixation system of FIG. 3 according to one of various examples, taken along line 6-6 of FIG. 3, illustrating at least one lead of an electrode secured to the anatomy.

In another of various examples, with reference to FIG. 14, an electrode fixation system 200f can include a first or bottom plate 208f and a second or top plate 210f. As the bottom plate 208f and top plate 210f can be similar to the bottom plate 208 and top plate 210 described with regard to FIGS. 3-5, only the differences between the bottom plate 208f and the bottom plate 208, and the top plate 210f and the top plate 210 will be discussed in great detail herein, and the same reference numerals will be used to denote the same or similar components.

With continued reference to FIG. 14, the bottom plate 208f can include a coupling member or post 238f. The post 238f can include a first member 280 and a second member 282, which can be separated by a slot 284. The first member 280 and second member 282 can be resilient, yet flexible, so that the first member 280 and second member 282 can each move relative to the other during the assembly of the top plate 210f to the bottom plate 208. In one example, the first member 280 and second member 282 can each include a lip 286, which can extend beyond the top surface 230 of the top plate 210f when the top plate 210 is assembled to the bottom plate 208. The lip 286 can secure the top plate 210f to the bottom plate 208, and can also cooperate with the top plate 210f to provide a compressive force on the at least one lead 202.

The top plate 210f could have a radius R, which can be smaller than a radius R1 of the bottom plate 208, but larger than a radius R2 measured from a perimeter 236f of the at least one bore 236 to the centerline C of the bottom plate 208. In other words, the top plate 210f can have a perimeter P that can be sized so that as the top plate 210f is coupled to the bottom plate 208f, the perimeter P of the top plate 210f at least partially occludes the at least one bore 236 of the bottom plate 208f. Thus, the size of the top plate 210f alone could be used to secure, fix or couple the at least one lead 202 to the cranium 108, if desired.

In this regard, the top plate 210f can be moved from a first position in which the top plate 210f is disassembled from the bottom plate 208f to a second position in which the top plate 210*f* is assembled with or coupled to the bottom plate 208*f*. As the top plate 210*f* moves from the first position to the second position, the perimeter P of the top plate 210*f* can occlude the at least one bore 236 of the bottom plate 208*f*, thereby frictionally locking at least one lead 202 to the anatomy.

Therefore, the various electrode fixation systems 200 of the present disclosure can enable a user or surgeon to couple, secure or fix a lead 202 of at least one electrode to a cranium 108. In addition, it should also be noted that while the post 236 is described and illustrated herein as being formed on the first or bottom plate 208, the post 236 could be formed on either the bottom plate 208 or the top plate 210, and the coupling bore 254 could be formed in the other of the bottom plate 208 or the top plate 210. The bottom plate 208 and the top plate 210 of the electrode fixation systems 200 can cooperate to enable the surgeon to evaluate the placement of the at least one electrode within the cranium 108 at a later time, which can be desirable in certain neurosurgical procedures.

In this regard, the surgeon can guide a deep brain stimulator (DBS) electrode to a desired position in an anatomy for electrical stimulation of the anatomy. Then, the surgeon can couple, secure or fix the lead of the at least one DBS electrode relative to the anatomy with one of the electrode fixation systems 200. At a later time, such as after the patient 16 has recovered from the procedure, the surgeon can re-evaluate the effectiveness of the electrical stimulation within the anatomy. If at that time the surgeon determines that the electrode stimulation is appropriate, the surgeon can complete the neurosurgical procedure by permanently fixing the lead of the at least one electrode to the anatomy, with the electrode fixation system 200 or with another device. Alternatively, if the surgeon determines the electrical stimulation is not effective, then the electrical fixation system 200 allows the surgeon to easily uncouple the lead of the at least one electrode from the anatomy so that the at least one electrode can be re-positioned within the anatomy.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. Therefore, it is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. A system adapted to secure at least one electrode to an anatomy comprising:
    a first plate that includes at least one first passage configured to receive a lead of the at least one electrode;
    a second plate configured to move relative to the first plate;
    a coupling member in the form of a post having a pitch that extends from a surface of the first plate or a surface of the second plate;
    a coupling bore that cooperates with the post, the coupling bore formed in the other of the first plate or the second plate; and
    the second plate including at least one second passage that is coaxially aligned with the at least one first passage when the second plate is in a first position relative to the coupling member and is offset from the at least one first passage when the second plate is moved to a second position relative to the coupling member;
    wherein movement of the coupling bore on the post from the first position to the second position rotates the second plate relative to the first plate to cause the second plate to occlude the at least one first passage of the first plate so as to be adapted to secure the lead of the at least one electrode to the anatomy.

2. The system of claim 1, wherein the movement of the second plate relative to the first plate couples the second plate to the first plate.

3. The system of claim 1, further comprising:
    a base ring that includes at least one flange and a bore, the at least one flange configured to receive at least one fastener so as to be adapted to couple the base ring to the anatomy and the bore includes a shoulder that retains the first plate and the second plate within the bore, the bore positionable over an access hole formed in the anatomy; and
    a cover that is releasably coupled to the base ring to substantially enclose the bore, the first plate and the second plate.

4. The system of claim 3, wherein the base ring defines at least one guide to direct the at least one lead out of the bore of the base ring.

5. The system of claim 1, wherein in the first position, the second plate does not occlude the at least one first passage of the first plate.

6. The system of claim 1, wherein the at least one first passage comprises at least one closed circular bore.

7. A system adapted to secure at least one electrode to an anatomy comprising:
    a base ring that includes at least one flange that is adapted to couple the base ring to the anatomy, and a bore positionable over an access hole formed in the anatomy for enabling at least one instrument to pass through the bore into the anatomy;
    a first plate that includes at least one first passage and a coupling member that extends from a surface of the first plate, the first plate at least partially received within the bore of the base ring;
    a second plate that includes a coupling feature that cooperates with the coupling member and at least one second passage that is coaxially aligned with the at least one first passage when the second plate is in a first position relative to the coupling member and is offset from the at least one first passage when the second plate is moved to a second position relative to the coupling member, the second plate at least partially received within the bore of the base ring in the second position; and
    a cover that is releasably coupled to the base ring to substantially enclose the bore, the first plate and the second plate when the second plate is in the second position;
    wherein the movement of the second plate to the second position at least partially occludes the at least one first passage of the first plate;
    wherein the second plate is uncoupled from the first plate in the first position and is coupled to the first plate in the second position.

8. The system of claim 7, wherein the at least one instrument is selected from the group comprising a microelectrode, a semi-microelectrode, a macroelectrode, a deep brain stimulator (DBS) electrode and combinations thereof.

9. The system of claim 8, wherein the at least one instrument is slidably received through the at least one first passage and the at least one second passage and the movement of the second plate into the second position is adapted to couple the at least one instrument to the anatomy.

10. The system of claim 7, wherein the at least one first passage and the at least one second passage each comprise at least one closed circular bore.

11. The system of claim 7, wherein the second plate rotates about an axis to move from the first position to the second position.

12. A method of securing at least one electrode to an anatomy comprising:
positioning at least one first plate having at least one first passage about an opening formed in the anatomy, the first plate including a post extending therefrom, the post having a pitch;
positioning a lead of at least one electrode through the at least one first passage of the first plate;
positioning the at least one electrode within the anatomy with the lead of the at least one electrode extending from the opening; and
coupling a second plate to the first plate, the second plate including a coupling bore configured to cooperate with the post and at least one second passage that is coaxially aligned with the at least one first passage when the second plate is in a first position relative to the post and is offset from the at least one first passage when the second plate is moved to a second position relative to the post, wherein coupling the second plate to the first plate includes:
receiving the post in the coupling bore and moving the second plate on the post from the first position to the second position so as to rotate the second plate relative to the first plate via the pitch of the post to cause the second plate to at least partially occludes the at least one first passage of the first plate to couple the lead of the at least one electrode to the first plate.

13. The method of claim 12, wherein positioning at least one electrode within the anatomy further comprises:
positioning at least one of a microelectrode, a semi-microelectrode, a macroelectrode, a deep brain stimulator (DBS) probe or combinations thereof within the anatomy.

14. The method of claim 12, wherein coupling the second plate to the first plate further comprises:
coupling the second plate to the first plate so that a wall of the at least one second passage formed in the second plate at least partially occludes the at least one first passage of the first plate.

* * * * *

UNITED STATES PATENT AND TRADEMARK OFFICE
CERTIFICATE OF CORRECTION

| | | |
|---|---|---|
| PATENT NO. | : 8,417,353 B2 | Page 1 of 1 |
| APPLICATION NO. | : 12/432291 | |
| DATED | : April 9, 2013 | |
| INVENTOR(S) | : Appenrodt et al. | |

It is certified that error appears in the above-identified patent and that said Letters Patent is hereby corrected as shown below:

In the Claims

<u>Column 18, line 12, Claim 12:</u> "plate to at least partially occludes the" should correctly read -- plate to at least partially occlude the --.

Signed and Sealed this
Tenth Day of February, 2015

Michelle K. Lee
*Deputy Director of the United States Patent and Trademark Office*